United States Patent [19]

Garcia

[11] Patent Number: 4,488,541

[45] Date of Patent: Dec. 18, 1984

[54] THERAPEUTIC ADAPTER

[76] Inventor: Juan A. S. Garcia, P.O. Box 36805, Houston, Tex. 77236

[21] Appl. No.: 448,249

[22] Filed: Dec. 9, 1982

[51] Int. Cl.³ .......... A61F 5/00

[52] U.S. Cl. .......... 128/79; 128/138 R

[58] Field of Search .......... 128/79, 132 R, 138, 128/386

[56] References Cited

U.S. PATENT DOCUMENTS

| | | | |
|---|---|---|---|
| D. 246,119 | 10/1977 | Okamoto | 128/132 R X |
| 745,264 | 11/1903 | Todd | 128/138 R |
| 2,559,059 | 7/1951 | Worstenholm | 128/79 |
| 4,381,000 | 4/1983 | Duncan | 128/79 |

FOREIGN PATENT DOCUMENTS

| | | | |
|---|---|---|---|
| 491522 | 8/1927 | Fed. Rep. of Germany | 128/79 |
| 2460812 | 7/1976 | Fed. Rep. of Germany | 128/79 |
| 336941 | 4/1959 | Switzerland | 128/79 |

*Primary Examiner*—Dalton L. Truluck
*Attorney, Agent, or Firm*—Hubbard, Thurman, Turner & Tucker

[57] ABSTRACT

Disclosed is a therapeutic sex aid adapter. The adapter includes a flexible pubic shield having a plurality of monolithically formed inverted conical projections. The adapter may also include a monolithically formed tubular portion. The adapter is held in place by a system of waist and leg belts.

15 Claims, 3 Drawing Figures

THERAPEUTIC ADAPTER

BACKGROUND OF THE INVENTION

A. Field of the Invention

The present invention relates generally to sex aid devices, and more particularly to a therapeutic sex aid adapter for increasing male potency and female enjoyment during sexual intercourse.

B. Description of the Prior Art

Sexual intercourse is generally regarded as being necessary for the normal enjoyment of life and is particularly important in the maintenance of a happy and healthy relationship being married people. It is also generally well known that sexual intercourse provides a healthy combination of stimulation and relaxation, much like jogging or other forms of exercise, that increases fitness and general well being.

Unfortunately, it is also well known that a number of people, because of sexual disfunction or incompatibility, do not enjoy the full benefits of sexual intercourse. For example, some men are incapable of providing the intensity or duration of stimulation necessary to make sexual intercourse enjoyable and satisfying for the female partner. Such enability is generally referred to sexual incompatibility and is a common source of tension between couples. Additionally, some men are unable to attain or maintain an erection, and are thus unable to perform sexual intercourse. The enability to attain or maintain erection is commonly called impotence and the problems associated therewith are obvious and well known.

There have been developed a number of devices for increasing male potency or enhancing general sexual enjoyment. For example, U.S. Pat. Nos. 3,149,629, and 3,626,931, disclose electro mechanical vibrator apparatus for use during sexual intercourse to provide additional stimulation to the female. U.S. Pat. Nos. 3,633,572; 4,206,752; 4,224,933, disclose what may be called passive stimulator devices which are worn by the male and provide additional stimulation to the female. Additionally, the '572 and '933 patents, along with U.S. Pat. No. 3,401,687 disclose devices which restrict blood flow from the penis, thereby to prolong and maintain erections. U.S. Pat. Nos. 1,511,572, and 4,022,196, disclose strap-on prosthetic devices which are adapted to provide support to a flaccid penis thereby to enable completely impotent males to perform sexual intercourse. U.S. Pat. No. 3,920,007, discloses an alternative aid for enabling impotent men to have intercourse. U.S. Pat. No. 3,773,040 discloses an alternative blood flow restricting device.

It is an object of the present invention to provide an improved device for increasing sexual enjoyment. A further object of the invention to provide an improved device for increasing male potency. It is a further object of the invention to provide an improved device for enhancing female enjoyment during intercourse.

SUMMARY OF THE INVENTION

Briefly stated, the foregoing and other objects are accomplished by the device of the present invention. The device includes a flexible pubic shield that is adapted to fit directly above and partially about the penis of a male wearer. The pubic shield includes a plurality of monolithically formed projections located so as to provide clitoral and vaginal contact during intercourse, thereby to increase female stimulation. The bottom margin of the pubic shield is formed to define a semicircular notch which fits partially about the base of the penis.

The pubic shield preferably includes a monolithically formed tubular portion having a top semicylindrical section that is contiguous with the notch and extends generally perpendicularly from the pubic shield. The tubular portion also includes a monolithically formed lower semicylindrical section that is attached along one side to the upper semicylindrical portion. The other side of the lower semicylindrical section is detachably attachable to the other side of the upper semicylindrical section, thereby to completely encircle the base portion of the penis. The lower semicylindrical section is preferably more flexible and elastic than the upper semicylindrical section and the lower semicylindrical section may be attached to the upper semicylindrical section at different placs, thereby to accomodate different diameter penises or to increase the tightness of fit. The tubular portion preferably includes a plurality of radially outwardly projecting fingers which increase vaginal stimulation during intercourse. The tubular portion may be of different lengths depending on the needs of the wearer and may be eliminated entirely if desired.

The device is held in position by means of a system of waist and leg belts. Preferably, the system includes a first belt that is attached semifixedly adjacent one side margin of the pubic shield and is detachably attachable adjacent the other side margin of the shield. Preferably, the middle portion of the first belt is slidingly attached to the pubic shield adjacent the first side margin. The first belt thus provides a leg loop defined between the point of semifixed attachment and sliding attachment on the first side margin and a waist lopp defined between the sliding attachment on the first side margin and the detachable attachment on the second side margin. A complimentary second belt is attached so as to provide a leg loop adjacent the other side margin and a corresponding waist loop. The belt system of the device of the present invention provides improved stability to the device during use.

DESCRIPTION OF THE PREFERRED EMBODIMENT

Figure 2:
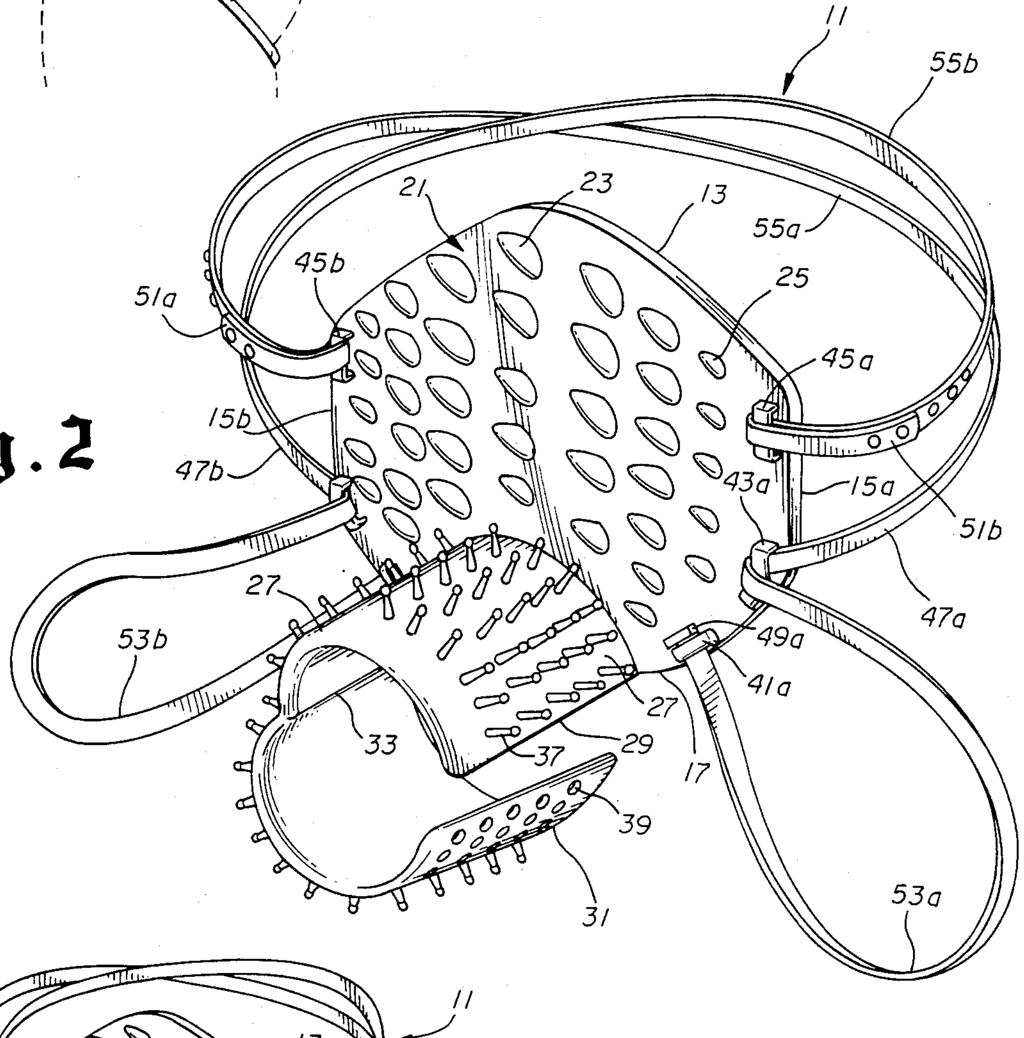
FIG. 2 is a perspective view of a preferred embodiment of the device of the present invention.
Figure 3:
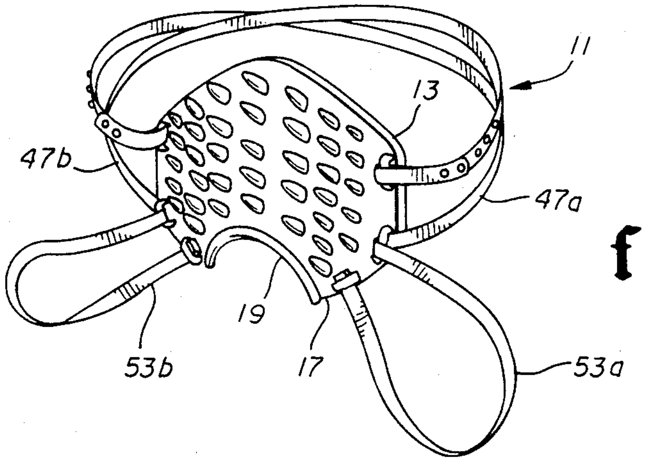
FIG. 3 is a perspective view of an alternative embodiment of the device of the present invention.

Referring now to the drawing, and first to FIG. 2, the device of the present invention is designated generally by the numeral 11. Device 11 includes a thick flexible pubic shield formed, preferably, from a flexible plastic material. Pubic shield 13 is shaped and sized to conform generally to the pubic area of a typical adult male and includes, generally, a left side margin **15*a* and a right side margin 15*b*. Pubic shield 13 also includes, generally, a bottom margin 17 which is formed to define a semicircular notch 19, which is best shown in FIG. 3**, adapted to fit partially about the base of the penis.

Pubic shield 13 includes a plurality of monolithically formed inverted conical projections designated generally by the numeral 21. The field of conical projections 21 includes generally a central plurality of projections, including a projection 23, which are of relatively large size and are positioned to provide clitoral stimulation during intercourse. The field of conical projections 21 also includes smaller marginal projections, including a projection 25, which are adapted to provide additional stimulation during intercourse.

Device 13, in the preferred embodiment, includes a tubular portion 27 formed monolithically with and projecting generally perpendicular to pubic shield 13. Tubular portion 27 includes an upper semicylindrical section 29 that is contiguous with notch 19. Tubular portion 27 also includes a lower semicylindrical section 31 which is formed monolithically with upper semicylindrical section 29 and attached thereto along a line 33 The other side of lower semicylindrical section 31 is detachably attachable to the other side of upper semicylindrical section 29, thereby to encircle and fasten about the penis, shown in phantom in FIG. 1 and designated by the numeral 35. The detachable attachment is achieved by means of the interaction of a plurality of knob-headed flexible fingers 37 formed monolithically on upper semicylindrical section 29 and a plurality of holes 39 formed in lower semicylindrical section 31. In use, lower semicylindrical section 31 is drawn tightly about the penis and the knob-headed fingers 37 are snapped into holes 39. In the preferred embodiment, lower semicylindrical section 31 is thinner and therefore more flexible and elastic than upper semicylindrical section 29, which has a sloping forward edge. A plurality of substantially parallel and adjacent rows of holes 39 are provided so as to be positionable over different rows of knob-headed fingers 37, thereby to make the diameter of tubular portion 27 variable so as to accomodate different diameter penises or increase or decrease the constriction of the penis. In the preferred embodiment, the knob-headed fingers 37 substantially completely cover the exterior of tubular portion 27 thereby to provide additional vaginal stimulation during intercourse.

The length of tubular portion 27 may be variable according to the needs of the user. For example, men who are unable to achieve an erection, will require a relatively long tubular portion 27 to provide sufficient support and rigidity for penetration. Men who can achieve erection may use a shorter tubular projection 27 for the purpose of restricting blood flow, thereby prolonging erection and enhancing vaginal stimulation. Some men may prefer to use the device of the invention without any tubular portion, as shown in FIG. 3.

Device 11 is stabilized and held in position during use by a system of belts anchored to pubic shield 13. Pubic sheld 13 has preferably formed thereon two sets of anchor attachments. The first set of anchor attachments is formed adjacent left side margin 15*a* and includes a bottom anchor attachment 41*a*, a central anchor attachment 43*a*, and a top anchor attachment 45*a*. A corresponding set of anchor attachments 41*b*, 43*b* and 45*b* are provided adjacent right side margin 15*b*.

The belt and anchor system also includes a first belt 47*a* and a second belt 47*b*. First belt 47*a* includes at one end a stop 49*a* which is formed to retain the end of first belt 47*a* semifixedly with bottom anchor attachment 41*a*. The middle portion of first belt 47*a* is slidingly run through central anchor attachment 43*a*. The other end 51*a* of belt 47*a* is adapted for detachable attachment to top anchor attachment 45*b* adjacent right side margin 15*b*. Belt 47*a* thus defines between bottom anchor attachment 41*a* and central anchor attachment 43*a* a left leg loop 53*a*, and between central anchor attachment 43*a* and top anchor attachment 45*b* a waist loop 55*a*. Second belt 47*b* is arranged similarly, but in mirror image fashion, to define a right leg loop 53*b* and a second waist loop 55*b*.

Figure 1:
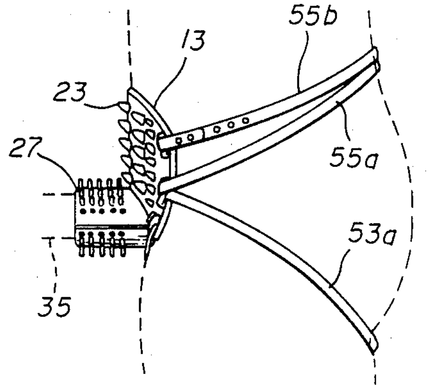
FIG. 1 is an elevation view showing a preferred embodiment of the present invention and its intended environment.

In use, the male user puts on apparatus 11 by positioning waist loops 55*a* and 55*b* about his waist and putting his left leg through left leg loop 53*a* and his right leg through right leg loop 53*b*, generally as shown in FIG. 1. The attached lengths of belts 47*a* and 47*b* may be adjusted by means of snaps 51*a* and 51*b* or the like thereby to properly position and stabilize pubic shield 13 on the wearer. The wearer may then, if he is using the embodiment of FIG. 2, properly tighten tubular portion 27 or, if using the embodiment of FIG. 3, proceed directly to intercourse.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth or shown in the accompany drawings is to be interpreted as illustrative and not in a limiting sense.

What is claimed is:

1. A therapeutic adapter for use by a male wearer, which comprises:

a sheetlike flexible pubic shield having bottom and side margins, said bottom margin being formed to define a semicular notch adapted to partially surround the base of the penis of said male wearer;

a plurality of projections affixed to one side of said pubic shield;

a tubular portion attached to said pubic shield and projecting away from said pubic shield in the same direction as said plurality of projections, said tubular portion having an upper semicylindrical section attached to said pubic shield around said notch, and a lower semicylindrical section attached along one side thereof to one side of said upper tubular portion and means for detachably attaching the other side of lower semicylindrical section to the other side of said upper semicylindrical section;

and means for attaching said pubic shield to said male wearer with said notch positioned partially around the base of the penis of said male wearer with said projections projecting away from said male wearer.

2. The therapeutic adapter as claimed in claim 1, wherein said tubular portion includes a plurality of radially projecting flexible fingers.

3. The therapeutic adapter as claimed in claim 1, wherein said upper and lower semicylindrical sections each include a plurality of radially projecting flexible fingers.

4. The therapeutic adapter as claimed in claim 1, wherein said detachably attaching means is adjustable to accomodate different diameter penises.

5. The therapeutic adapter as claimed in claim 1, wherein one of said semicylindrical sections includes a row of knob-headed fingers attached thereto adjacent said other side thereof and the other of said semicylindrical sections includes a row of holes formed therein adjacent said other side thereof, said knob-headed fingers being engageable with said holes to define said detachable attaching means.

6. The therapeutic adapter as claimed in claim 5, wherein said one of said semicylindrical sections includes a second row of knob-headed fingers and said other of said semicylindrical sections includes a second row of holes formed therein, whereby said semicylindrical sections may be detachably attached at two positions to accommodate different diameter penises.

7. The therapeutic adapter as claimed in claim 1, wherein said plurality of projections includes a multiplicity of first projections positioned above said semicircular notch and a multiplicity of second projections positioned on either side of said first projections.

8. The therapeutic adapter as claimed in claim 7, wherein said first projections are larger than said second projections.

9. The therapeutic adapter as claimed in claim 1, wherein said means for attaching said pubic shield to said male wearer includes belt means attached to said pubic shield for encircling the waist of said male wearer.

10. The therapeutic adapter as claimed in claim 9, wherein said means for attaching said pubic shield to said male wearer includes other belt means attached to said pubic shield for encircling each leg of said male wearer.

11. A therapeutic adapter for use by a male wearer, which comprises:

a sheetlike flexible pubic shield having bottom and side margins, said bottom margin being formed to define a semicircular notch adapted to partially surround the base of the penis of said male wearer;

a plurality of projections affixed to one side of said pubic shield;

and means for attaching said pubic shield to said male wearer with said notch positioned partially around the base of the penis of said male wearer with said projections projecting away from said male wearer, said means for attaching said pubic shield including;

a first belt having an end attached adjacent one side margin of said pubic shield;

means for attaching the middle portion of said first belt adjacent said one side margin of said pubic shield to define a first leg loop;

means for attaching the other end of said first belt adjacent the other side margin of said pubic shield to define a first waist loop;

a second belt having an end attached adjacent said other side margin of said pubic shield;

means for attaching the middle portion of said second belt adjacent said other side margin of said pubic shield to define a second leg loop;

and means for attaching the other end of said second belt adjacent said one side margin of said pubic shield to define a second waist loop.

12. A therapeutic adapter, which comprises:

a unitary flexible sheetlike pubic shield having bottom and side margins, said pubic shield including a plurality of monolithically formed inverted conical projections on one side thereof, said pubic shield including adjacent each side margin a monolithically formed bottom anchor, a monolithically formed center anchor, and a monolithically formed top anchor, said bottom margin being formed to define a semicircular notch;

a first belt having one end attached to said bottom anchor adjacent one side margin of said pubic shield, with the middle portion of said first belt being attached to said center anchor adjacent said one side margin and the other end of said first belt attachable to said top anchor adjacent the other side margin;

and a second belt having one end attached to said bottom anchor adjacent said other side margin of said pubic shield, with the middle portion of said second belt being attached to said center anchor adjacent said other side margin and the other end of said second belt attachable to said top anchor of said one side margin.

13. The therapeutic adapter as claimed in claim 12, including a monolithically formed tubular portion having an upper semicylindrical section having an end contiguous with said notch and projecting from said pubic shield, said tubular portion including a monolithically formed lower semicylindrical section attached along one side to said upper tubular section and detachably attachable along the other side of said upper tubular section.

14. The therapeutic adapter as claimed in claim 13, wherein said lower semicylindrical section is formed to be more flexible than the said upper semicylindrical section.

15. The therapeutic adapter as claimed in claim 13, wherein said tubular portion includes a plurality of radially outwardly projecting monolithically formed flexible fingers.

* * * * *